United States Patent
Göhring

[11] Patent Number: 5,914,404
[45] Date of Patent: Jun. 22, 1999

[54] PROCESS FOR THE PREPARATION OF QUINARGINE

[75] Inventor: Wolfgang Göhring, Steinen, Germany

[73] Assignee: Hoffmann-La Roche Inc., Nutley, N.J.

[21] Appl. No.: 08/896,354

[22] Filed: Jul. 18, 1997

[30] Foreign Application Priority Data

Aug. 9, 1996 [EP] European Pat. Off. ............... 96112866

[51] Int. Cl.⁶ ..................... C07D 215/36; C07D 215/38
[52] U.S. Cl. ............................................ 546/169; 546/170
[58] Field of Search .................................. 546/169, 170

[56] References Cited

U.S. PATENT DOCUMENTS 5,480,887  1/1996  Hornback et al. ...................... 514/301

FOREIGN PATENT DOCUMENTS

| | | |
|---|---|---|
| 0 346 847 | 12/1989 | European Pat. Off. . |
| 0 432 694 | 6/1991 | European Pat. Off. . |
| 0 432 695 | 6/1991 | European Pat. Off. . |
| 0 611 774 | 8/1994 | European Pat. Off. . |
| 0635 493 | 1/1995 | European Pat. Off. . |
| WO 94/17096 | 8/1994 | WIPO . |
| WO 95/20962 | 8/1995 | WIPO . |

OTHER PUBLICATIONS

G.W. Anderson, et al., The Use of Esters of N–Hydroxysuccinimide in Peptide Synthesis, J. Am. Chem. Soc., vol. 86, pp. 1839–1842 (1964).

J.W. Davis, Studies with Quinolines. I. Synthesis of Quinaldic Acid and Some of Its Amide Derivatives, J. Org. Chem., vol. 24, pp. 1691–1694 (1959).

P. Stelzel, Methoden der organischen Chemie; Synthese von Peptiden, vol. 15, part 2, pp. 214–259 (1974).

G. Wendelberger, Methoden der organischen Chemie; Synthese von Peptiden, vol. 15, part 2, pp. 130–169 (1974).

Chemical Abstracts 120:245780, 1993.

Chemical Abstracts 115:183974, 1991.

*Primary Examiner*—D. Margaret M. Mach
*Attorney, Agent, or Firm*—George W. Johnston; William H. Epstein; Briana C. Buchholz

[57] ABSTRACT

The present invention is concerned with a novel process for the manufacture of quinargine

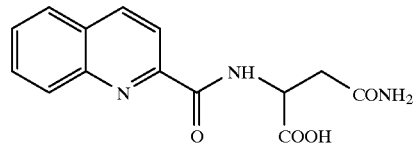

I (N-(2-quinolylcarbonyl)-asparagine) based on the reaction of the succinimide ester

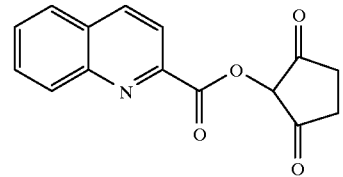

II with asparagine or asparagine salts in an aqueous reaction medium at a neutral pH value.

7 Claims, No Drawings

PROCESS FOR THE PREPARATION OF QUINARGINE

BACKGROUND OF THE INVENTION

Quinargine is a valuable intermediate for the manufacture of pharmacologically active compounds. Thus, as set for in European Patent Application No. 611,774, quinargine can be converted into pharmacologically active compounds which are primarily suitable for the treatment of viral infection, especially of such infections which are caused by HIV or other retroviruses.

Various reaction routes have been described for the manufacture of quinaldic acid derivatives. For example, Davis describes the reaction, which normally proceeds in good yields, of quinaldic acid chloride with primary and secondary amines, amino acids and amino acid esters under Schotten-Baumann conditions (J. Am. Chem. Soc. (1959), 24, 1691–1694). In the Schotten-Baumann reaction the substance to be acylated in 10% sodium hydroxide solution is shaken with an acid chloride until this has been consumed. The reaction is carried out using a large excess of alkali and acid chloride. However, in the manufacture of quinargine and its derivatives this procedure leads; only to moderate yields.

Anderson et al. describe the use of N-hydroxysuccinimide esters in peptide syntheses (Anclerson et al. (1964) J. Am. Chem. Soc. 86, 1839–1842). Having regard to the greater water solubility, these esters are generally better suited, for the synthesis than the corresponding N-hydroxyphthalimide esters. The preparation of N-acyl-amino acid N-hydroxysuccinimide esters is generally effected by reacting an N-acyl-amino acid with N-hydroxysuccinimide according to the mixed anhydride method, particularly using dicyclohexylcarbodiimide (P. Stelzel in Houben-Weyl: "Methoden der organischen Chemie; Synthese von Peptiden", volume 15, part 2, p. 214, (1974)). The N-hydroxy-succinimide esters are then reacted with the corresponding amino acids in an organic-aqueous solvent mixture.

Wendlberger also describes the use of hydroxysuccinimide esters in the synthesis of peptides (Houben-Weyl: "Methoden der organischen Chemie; Synthese von Peptiden", volume 15, part 2 p. 130 (1974)). The high aminolysability of the N-hydroxy-succinimide esters compared with the low sensitivity to hydrolysis and alcoholysis enables peptide syntheses to be carried out not only in organic solvents, but also in organic-aqueous solvent mixtures such as ethanol/water, dioxan/water etc. Peptide syntheses with N-hydroxysuccinimide esters can also be carried out in a two-phase system such as dichloro-methane/water, etc.

The manufacture of 2S-N-(quinolin-2-ylcarbonyl)amino-3-oxo-3-aminopropanoic acid is described in International Patent Application WO95/20962. Here, the reaction of the corresponding pentafluorophenyl ester with asparagine is effected in a dioxanwater mixture.

All of the aforementioned processes have considerable disadvantages when they are used for the manufacture of quinargine. Thus, the reaction proceeds with yields which are far from quantitative. This is primarily due to the formation of a byproduct by hydrolysis. Consequently, the reaction mixture has to be subjected to an expensive working-up. Moreover, problematic byproducts such as the toxic pentafluorophenol (WO95/20962) result during the manufacture of quinargine and, respectively, quinargine derivatives, so that the large-scale manufacture using methods of the state of the art can not be achieved satisfactorily.

SUMMARY OF THE INVENTION

This invention is directed to a process for the manufacture of quinargine of formula I

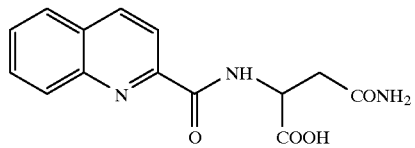

which process comprises reacting succinimide ester derivatives of formula II

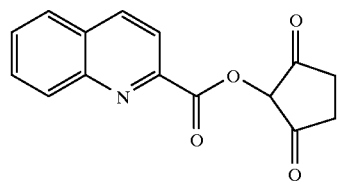

with asparagine or asparagine salts in an aqueous medium at a neutral pH value.

DETAILED DESCRIPTION OF THE INVENTION

The present invention for the manufacture of quinargine (n-(1-quinolylcarbonyl)-asparagine) of formula I

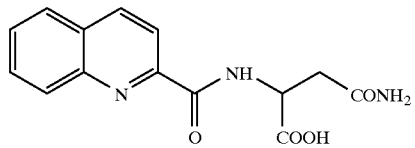

is based on the reaction of succinimide ester of formula II

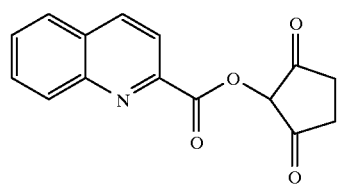

with asparagine or asparagine salts in an aqueous reaction medium at a neutral pH value to produce quinargine.

The process is suitable for the manufacture of S- and R-quinargine. S- or R-quinargine is obtained depending on the asparagine or asparagine salt which is used.

The corresponding starting materials of formula II are known and can be prepared, for example, according to the method described by Anderson et al. (loc. cit.). The preparation of the succinimide ester is effected, for example, by reacting the quinalolic acid with N-hydroxysuccinimide with the addition of dicyclohexylcarbodiimide.

The process in accordance with the invention comprises reacting the succinimide ester of formula II in aqueous medium at an approximately neutral pH value.

Advantageously, the reaction should take place at a pH value between 6 and 8, preferably at a pH value of about 7. The neutral pH value can be achieved by adjusting the reaction medium through the addition of conventional buffer systems, for example carbonate or phosphate buffer. An aqueous sodium hydrogen carbonate solution is preferred.

In carrying out this reaction, temperature and pressure are not critical. The reaction of the N-succinimide ester of formula II is advantageously effected at about 20 to 70° C. preferably at 50° C. Reaction to produce quinargine can be achieved in a period of to 2 to 8 hours, with on average a reaction time key with 2.5 hours being sufficient for the quantitative conversion.

For the working-up of the reaction bath, methanol and concentrated hydrochloric acid are added at an elevated temperature. The concentrated hydrochloric acid is added in measured amounts such that the pH is adjusted to about 2.5 to 3. Advantageously, the addition of an about equimolar amount of HCl is effected at 30 to 70° C. preferably at 50° C. Subsequently, the reaction mixture is left to cool to 0 to 30° C. preferably to about 10° C. for about 2 to 8 hours, preferably 2.5 hours, at a constant cooling rate. Subsequently, the reaction product can be filtered off.

According to this procedure the reaction product of formula I is obtained in a yield of 90 to 93%, which is thus almost quantitative. No further purification is required for subsequent reactions, for example the manufacture of HIV inhibitors.

Furthermore, the present invention is concerned with the manufacture of pharmaceutically active substances. N-(2-quinolylcarbonyl)-L-asparagine can be reacted with 2-[3-(S)-amino-2(R)-hydroxy-4-phenylbutyl]-N-tertbutyl-decahydro-(4aS,8aS)-isoquinoline-3(S)-carboxamide, which is known from European Patent Application No. 635,493, in the presence of a coupling reagent such as e.g. a carbodimide and a N-hydroxy compound, with the N-hydroxy compound being used in a catalytic amount. As described in Example 7 of European Patent Application No. 611,774, the aforementioned substances can be converted in the presence of dicyclohexylcarbodiimide using a catalytic amount of 1-hydroxy-2(1H)-pyridone in an inert solvent or solvent mixture such as ethyl acetate/tetrahydrofuran into N-t-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide or into pharmaceutically suitable salts or corresponding esters derived therefrom. N-t-butyl-decahydro-2-[2(R)-hydroxy-4-phenyl-3(S)-[[N-(2-quinolyl-carbonyl)-L-asparaginyl]aminobutyl]-(4aS,8aS)-isoquinoline-3(S)-carboxamide and its aforementioned derivatives can be used as antiviral agents, especially as HIV inhibitors, as described in European Patent Applications Nos. 346,847 and 432,695.

Accordingly, the invention is also concerned with a process for the manufacture of these compounds. Such a process comprises in a first step the manufacture of a quinargine as described above. This substance is then converted in a subsequent step with 2-[3(S)-amino-2(R)-hydroxy-4-phenylbutyl]-N-tert.-butyl-decahydro-(4aS,8aS)-isoquinoline-3(S)-carboxamide into N-t-butyl-decahydro2-[2(R)-hydroxy-4-phenyl-3(S)-[[N-(2-quinolylcarbonyl)-L-asparaginyl]amino]butyl]-(4aS,8aS)-iso-quinoline-3(S)-carboxamide as described above or optionally into a corresponding salt, preferably the corresponding methane-sulphonate salt, or into an ester.

The following examples are illustrative but not limitative of the invention.

EXAMPLES

Example 1

Manufacture of S-quinargine 200 mg of quinaldic acid succinimide ester are reacted with 117 g of L-asparagine monohydrate under a weak stream of nitrogen and while stirring (600 r/min) for two hours in an aqueous sodium hydrogen carbonate solution (66 g in 1.5 litres). the internal temperature of the white suspension is increased from 20° C. to 50° C. with a constant heating rate within 2 ours. The white suspension thereby becomes light pink in color. In order to control the reaction, a sample can be tested by HPLC for the presence (<0.5%) of the quinaldic acid succinimide ester. The mixture is stirred at 50° C. for a further 0.5 hour. The reaction has then finished and 750 ml of methanol are added to the reaction mixture. After 5–10minutes the reaction mixture passes into solution almost completely. Then, about 90 ml of conc. hydrochloric acid are dosed in such that the pH of the reaction mixture is adjusted to 2.5–3. The white S-quinargine separates slowly. The stirring speed is maintained. The internal temperature rises from 50° C. to 54° C. When all of the hydrochloric acid has been added, the suspension is brought from 54° C. to 10° C. within 2.5 hours at a constant cooling rate and is stirred at this temperature for a further 0.5 hour. The suspension is filtered over an internal glass suction filter (10 cm diameter, porosity 3). The fairly large crystals permit a rapid filtration. The reactor is rinsed several times with the mother liquor, which is cooled to 10° C. The filter cake is subsequently washed three times with in each case a total of 300 ml of demineralized water. The filter cake is sucked dry and dried in vacuum oven (15–20 mbar) at 60° C. for 24 hours. Yield: 185.6–190.3 g (90–93%); purity ≧97%.

Example 2

Manufacture of R-quinargine

A procedure analogous to Example 1 is used. R-Quinargine is obtained with a content of >99% with a rotation of −50.1° C. (1% DMF) and a S-quinargine content of 0.1%.

I claim:

1. A process for the manufacture of quinargine of formula I

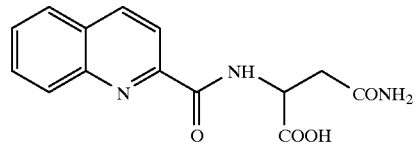

which process comprises reacting the succinimide ester of formula II

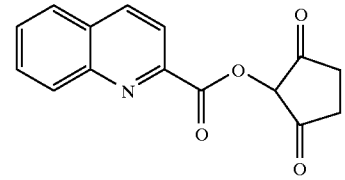

with asparagine or asparagine salts in an aqueous reaction medium at a neutral pH value to produce said quinargine.

2. A process in accordance with claim 1 wherein the reaction is carried out at a pH value between pH 6 and pH 8.

3. A process in accordance with claim 2, wherein said reaction medium is buffered with sodium hydrogen carbonate.

4. A process in accordance with claim 1, wherein the reaction is carried out at a temperature between 20 and 70° C.

5. A process in accordance with claim 1, wherein an equimolar amount of HCl in methanol is added in order to separate the reaction product.

6. A process in accordance with claim 5, wherein the HCl/methanol addition is effected at a temperature between 30 and 70° C.

7. A process for the manufacture of N-tert-butyl-decahydro-2[2(R)-hydroxy-4-phenyl-3(S)-[[N-(2-quinolyl-carbonyl)-L-asparaginyl]amino]butyl]-(4aS, 8aS)-isoquinoline-3(S)-carboxamide or of salts or esters derived therefrom, which process comprises a) the manufacture of N-(2-quinolylcarbonyl)-L-asparagine by reacting the succinimide ester of formula II

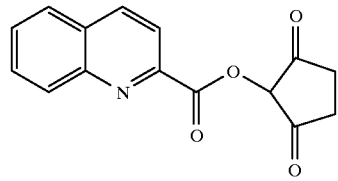

II with L-asparagine or L-asparagine salts in an aqueous reaction medium at a neutral pH value, and b) reacting the N-(2-quinolylcarbonyl)-L-asparagine obtained with 2-[3(S)-amino-2(R)-hydroxy-4-phenylbutyl]-N-tert-butyl-decahydro-(4aS,8aS)-isoquinoline-3(S)-carboxamide.

* * * * *

UNITED STATES PATENT AND TRADEMARK OFFICE
CERTIFICATE OF CORRECTION

PATENT NO. : 5,914,404
DATED : June 22, 1999
INVENTOR(S) : Wolfgang Göhring

Page 1 of 5

It is certified that error appears in the above-identified patent and that said Letters Patent is hereby corrected as shown below:

In claim 1, column 4, lines 50-58. Delete this formula:

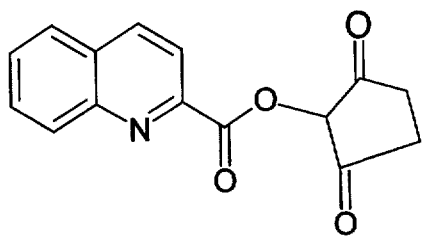

II

And replace it with the following formula shown below.

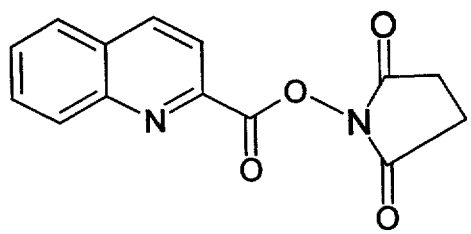

II

UNITED STATES PATENT AND TRADEMARK OFFICE
CERTIFICATE OF CORRECTION

PATENT NO. : 5,914,404
DATED : June 22, 1999
INVENTOR(S) : Wolfgang Göhring

It is certified that error appears in the above-identified patent and that said Letters Patent is hereby corrected as shown below:

In claim 7, column 6, lines 1-10. Delete this formula:

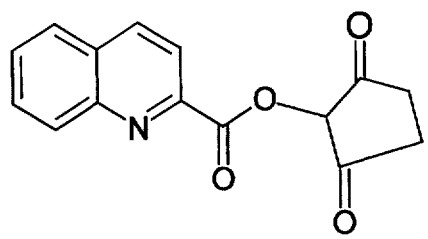

II

And replace it with the following formula shown below.

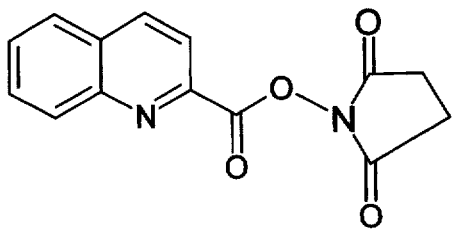

II

UNITED STATES PATENT AND TRADEMARK OFFICE
CERTIFICATE OF CORRECTION

PATENT NO. : 5,914,404
DATED : June 22, 1999
INVENTOR(S) : Wolfgang Göhring

It is certified that error appears in the above-identified patent and that said Letters Patent is hereby corrected as shown below:

In the abstract delete this formula:

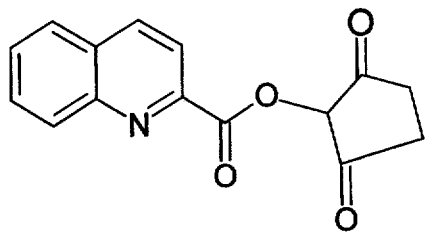

II

And replace it with the following formula shown below.

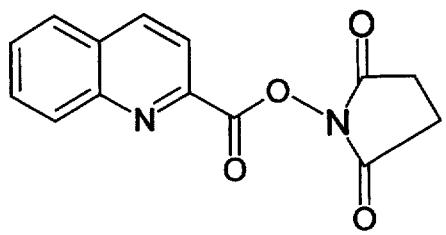

II

UNITED STATES PATENT AND TRADEMARK OFFICE
CERTIFICATE OF CORRECTION

PATENT NO. : 5,914,404
DATED : June 22, 1999
INVENTOR(S) : Wolfgang Göhring

It is certified that error appears in the above-identified patent and that said Letters Patent is hereby corrected as shown below:

In the summary of invention column 2, lines 15-25. Delete this formula:

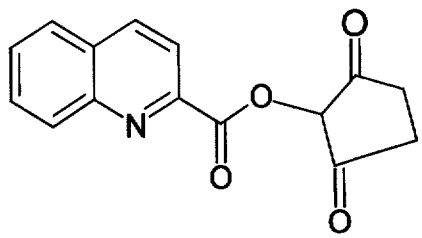

And replace it with the following formula shown below.

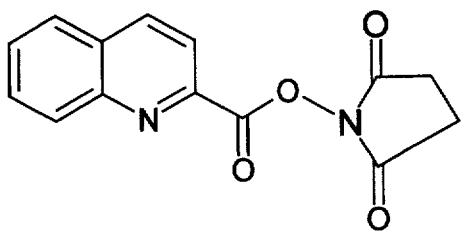

UNITED STATES PATENT AND TRADEMARK OFFICE
CERTIFICATE OF CORRECTION

PATENT NO. : 5,914,404
DATED : June 22, 1999
INVENTOR(S) : Wolfgang Göhring

It is certified that error appears in the above-identified patent and that said Letters Patent is hereby corrected as shown below:

In the detailed description of the invention, column 2, lines 45-53. Delete this formula:

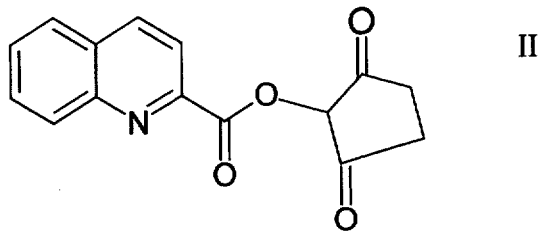

II

And replace it with the following formula shown below.

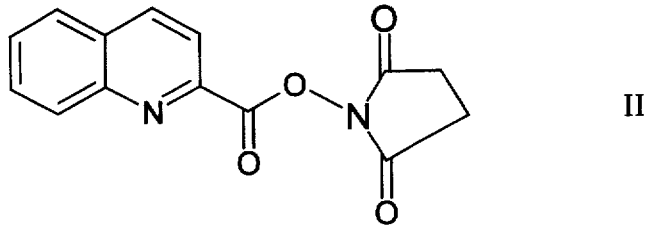

II

Signed and Sealed this

Fourth Day of January, 2000

Attest:

Attesting Officer

Acting Commissioner of Patents and Trademarks